United States Patent
Barthelmes et al.

(10) Patent No.: US 10,925,626 B2
(45) Date of Patent: Feb. 23, 2021

(54) SURGICAL INSTRUMENT HAVING A SPACING PIVOTING ELEMENT

(71) Applicant: Aesculap AG, Tuttlingen (DE)

(72) Inventors: Sven Barthelmes, Emmingen-Liptingen (DE); Dieter Weisshaupt, Immendingen (DE); Pedro Morales, Tuttlingen (DE); Daniel Morales, Tuttlingen (DE)

(73) Assignee: AESCULAP AG, Tuttlingen (DE)

( * ) Notice: Subject to any disclaimer, the term of this patent is extended or adjusted under 35 U.S.C. 154(b) by 129 days.

(21) Appl. No.: 16/308,550

(22) PCT Filed: Jun. 8, 2017

(86) PCT No.: PCT/EP2017/064016
§ 371 (c)(1),
(2) Date: Dec. 10, 2018

(87) PCT Pub. No.: WO2017/216039
PCT Pub. Date: Dec. 21, 2017

(65) Prior Publication Data
US 2019/0150965 A1    May 23, 2019

(30) Foreign Application Priority Data
Jun. 16, 2016    (DE) .................. 10 2016 111 001

(51) Int. Cl.
*A61B 17/28*    (2006.01)
*A61B 17/00*    (2006.01)
(Continued)

(52) U.S. Cl.
CPC .......... *A61B 17/2816* (2013.01); *A61B 17/28* (2013.01); *A61B 17/285* (2013.01);
(Continued)

(58) Field of Classification Search
CPC .... A61B 2017/2947; A61B 2017/2913; A61B 2017/00845; A61B 2017/0088;
(Continued)

(56) References Cited

U.S. PATENT DOCUMENTS 2,305,156 A    12/1942    Grubel
3,459,187 A *    8/1969    Pallotta .............. A61B 17/2816
                                                            606/208
(Continued)

FOREIGN PATENT DOCUMENTS

CN    103037787 A    4/2013
DE    10101425 A1    7/2002
(Continued)

OTHER PUBLICATIONS

Chinese Office Action for Chinese Application No. 201780042618.6, dated Jun. 14, 2019, with translation, 10 pages.
(Continued)

*Primary Examiner* — Jocelin C Tanner

(57) ABSTRACT

A surgical instrument includes a female instrument part that defines a hollow volume in a coupling region and a male instrument part that forms a guide section in the coupling region. The guide section is configured to at least partially pass through the hollow volume. A pivoting element, which has an upper section, a center section, and a lower section, couples the female instrument part and the male instrument part to each other in such a way that the female instrument part and male instrument part can pivot relative to each other about an axis of rotation of the pivoting element. A lateral upper contact step is formed between the upper section and the center section of the pivoting element and a lateral lower contact step is formed between the lower section and the center section of the pivoting element.

7 Claims, 2 Drawing Sheets

(51) Int. Cl.
*A61B 90/00* (2016.01)
*A61B 17/285* (2006.01)

(52) U.S. Cl.
CPC ............... *A61B 2017/0088* (2013.01); *A61B 2017/00845* (2013.01); *A61B 2017/2808* (2013.01); *A61B 2090/0813* (2016.02)

(58) Field of Classification Search
CPC ............ A61B 2017/2808; A61B 17/28; A61B 17/2816; A61B 17/285; A61B 17/282; A61B 17/2812
See application file for complete search history.

(56) References Cited

U.S. PATENT DOCUMENTS

2011/0313449 A1   12/2011   Cooper
2012/0029554 A1   2/2012    Kreidler
2014/0373689 A1*  12/2014   Sildve ...................... B25B 7/02
                                                        81/416
2018/0103995 A1*  4/2018    Ding ................... A61B 18/1442

FOREIGN PATENT DOCUMENTS

| DE | 202010010843 U1 | 12/2010 |
| DE | 202011000800 U1 | 5/2011 |
| DE | 202013010321 U1 | 1/2014 |
| EP | 2594210 A1 | 5/2013 |
| EP | 2873381 A1 | 5/2015 |

OTHER PUBLICATIONS

German Search Report for German Application No. 10 2016 111 001.9, dated Apr. 21, 2017, with translation—15 pages.
International Search Report and Written Opinion for Application No. PCT/EP2017/064016, dated Jul. 7, 2017—8 pages.

* cited by examiner

SURGICAL INSTRUMENT HAVING A SPACING PIVOTING ELEMENT

RELATED APPLICATIONS

This application is the United States national phase entry of International Application No. PCT/EP2017/064016, filed Jun. 8, 2017, which claims the benefit of priority of German Application No. 10 2016 111 001.9, filed Jun. 16, 2016. The contents of International Application No. PCT/EP2017/064016 and German Application No. 10 2016 111 001.9 are incorporated by reference herein in their entireties.

FIELD

The present invention relates to a surgical instrument comprising two instrument parts that can be swiveled relative to each other. Surgical instruments of the type according to the invention may be, for example, clamps, gripping devices, cutting devices and/or holding devices predominantly used in surgery and having any geometry, in particular scissors, grasping forceps and similar branch instruments.

BACKGROUND

Surgical instruments of the instrument branch type, which ensure a (scissor-like) relative movement of two instrument parts hinged to each other, are used in almost all medical fields. In order to allow the instrument parts to swivel in a plane manner, the instrument parts have contact surfaces that slide under friction when they swivel relative to each other, thus preventing the instrument parts from canting. Since the two instrument parts are usually made of the same material, there is a risk of the instrument parts seizing in the hinge area. This danger is further aggravated by manufacturing tolerances of the individual instrument parts, which lead to different contact surfaces in the assembled state. The resulting material wear, as well as a cold welding caused by friction, reduce the service life of surgical instruments. In addition, the operation of such a surgical instrument, which is subject to the highest requirements in terms of precision, is made more difficult by the above problems.

There are various documents that deal with mutually rubbing surfaces of surgical instruments. DE 10101425 A1, for example, discloses a surgical instrument with two instrument parts that can be swiveled towards each other. The problem underlying the above application is that it is difficult to clean and sterilize contact surfaces due to limited accessibility. In order to improve this accessibility, the construction of the instrument parts according to said publication is modified in such a way that outside their normal working zone, which refers to the usual angular spans of pivoting, they can be moved relative to each other in such a way that a face-to-face contact of the two instrument parts is removed in certain areas. This enables improved cleaning. Since the technical particularities mentioned in this document also result in surfaces rubbing against each other in a swivel area, the problem of seizure cannot be avoided.

Another generic document is represented by EP 2 594 210 A1. This document discloses a medical instrument in which two instrument parts are connected via a connecting pin (pivoting pin). A transverse groove in one of the two instrument parts causes the instrument parts to be movable relative to one another with a certain amount of clearance, which minimizes friction, in a state in which the instrument is not actively used. Since this clearance occurs only when the instrument is not actively used, it does not reduce the risk of seizure due to frequent use.

A third document shall be introduced by DE 20 2010 010 U1. Here too, a surgical instrument is disclosed which has two instrument parts that can be swiveled relative to each other and are exposed to the risk of seizure due to surface friction. The described mechanism for reducing this friction also refers only to a state in which the instrument is not actively used, which is why seizure cannot be reliably prevented in this way either.

SUMMARY

In view of this prior art, the present invention is based on the object of providing a surgical instrument of the branch type in which two instrument parts are aligned in a coupling/hinge area, i.e. an area in which two flat components (branches) in this area are swiveled relative to each other, in such a way that they are guided in a stable and robust manner (in order to avoid canting of the instrument parts) without having large contact surfaces in order to prevent seizing of the individual instrument parts.

From this embodiment according to the invention of the (upper) sides of the coupling/hinge area the following advantages can be derived, for example:
  The individual parts of the instrument are prevented from seizing, which increases the service life of the surgical instrument.
  By means of the predetermined contact surfaces of the individual instrument parts, which are reduced compared to the prior art and which are subject to significantly reduced tolerance fluctuations, the opening resistance is reduced/the instrument's run is improved and its service life is constant over a product chain.
  A process of lubricating the instrument can be carried out more efficiently in terms of time, as the need for lubricant per instrument becomes more uniform due to the smaller contact surfaces compared to the known prior art. This enables an efficient mechanical lubrication of the instrument, for example as part of a disinfection process.
  In addition, the disinfectability is optimized by the fact that the contact surfaces in the coupling/hinge area are more easily accessible and also smaller.
  The above-mentioned improvement of the instrument's run also increases the precision achievable by surgical intervention on the one hand and the ease of operation for the surgeon on the other.

The object of the present invention therefore relates in summary to a surgical instrument comprising two scissor-like coupled instrument parts (hinged to each other) which form at least one preferably flat/plane contact side in the area of their hinge connection/coupling, which more preferably also define/limit the maximum opening angle of the two instrument branches and on which the two instrument parts slide against each other when mounted.

In accordance with a first aspect of the present invention, at least one contact side of one or both instrument parts is provided with a flat material removal in the vicinity of the hinge connection/coupling, in such a way that a (planar) depression is formed in this region and at least one (planar) elevation is formed in the region more distant to the hinge connection/coupling. The elevation(s) form(s) the sliding surface for the opposite instrument part.

According to another aspect of the present invention, the hinge connection/coupling consists of a pin-like pivoting element or hinge pin with a center section which is thickened or radially widened relative to its axial end sections, or the hinge consists of a ring/sleeve pushed onto/slid onto the center section, whereby in both cases at least one, preferably two axially spaced axial stops/support edges are formed. The axial distance between the two axial stops is preferably dimensioned such that a (micro) gap results between the contact sides of the two instrument parts in the (unactuated) constructional position, so that, when the two instrument parts hinged to one another are pivoted, the sliding contact force between the instrument parts is reduced with respect to the prior art.

In more concrete terms, the surgical instrument of the present invention has preferably a first instrument part (female instrument part), which defines in a coupling/hinge region a preferably box-shaped hollow volume (push-through box), and a second instrument part (male instrument part), which in the coupling/hinge region forms a guide section (push-through section). This guide section is prepared to pass at least partially through the hollow volume (formation of a so-called push-through connection). The surgical instrument further has a pivoting element (hinge pin) with an upper end section, a center section and a lower end section, which couples the female instrument part and the male instrument part inserted into the hollow volume of the female instrument part to one another in the region of the hollow volume and the guide section in such a way that they can be pivoted relative to one another about an axis of rotation of the pivoting element. In this way, the two instrument parts are connected in such a way that they can be swiveled relative to each other while the branches are guided evenly.

Further preferred, a radially circumferential upper contact step/support edge is formed between the upper section and the center section of the pivoting element and a radially circumferential lower contact step/support edge is formed between the lower section and the center section of the pivoting element. These contact steps realize a spacing function of the pivoting element, as the radially circumferential steps/protrusions enable at least one abutment surface or stop for inner surfaces of the hollow volume of the female instrument part. This results in a constant (parallel) distance between two opposing inner surfaces of the hollow volume, between which the guide section of the male instrument part is slidably held, allowing robust and precise guidance of the two instrument parts relative to each other but preventing seizure of both instrument parts due to excessive contact forces between the two inner surfaces of the box-shaped hollow volume of the female instrument part and the guide section of the male instrument part.

It is also advantageous if the upper contact step is prepared to contact an upper inner surface of the hollow volume and/or the lower contact step is prepared to contact a lower inner surface of the hollow volume. Thus, the upper and/or lower step forms a geometrically predetermined contact surface for the respective inner surfaces of the hollow volume. These surfaces of the contact steps are preferably part of the center section of the pivoting element and may be designed/machined in such a way that contact surfaces between the two branches in the coupling/hinge area are sufficiently large for a robust guidance and at the same time sufficiently small to prevent seizure.

As soon as the guide section of the male instrument part has at least said one groove/depression which causes at least one gap between the male instrument part and the female instrument part, as has already been generally described above, this increases the advantages according to the invention. That gap causes a contact surface, which are herein referred to as guide surfaces, to be defined only in the region of the elevations and at least on the contact side with a groove/depression formed thereon, between the hollow volume or the two inner surfaces of the hollow volume, which are parallely spaced and predetermined for sliding guidance, and the guide section or the two contact sides, which are facing away from one another and predetermined for sliding guidance. The groove/depression can be formed freely and variably with regard to its geometry and depth, but can preferably be defined such that the resulting gap between the guide section of the male instrument part and the associated inner surface of the hollow volume of the female instrument part promotes the penetration of disinfectant. It is advantageous if the depth of the depression in relation to the respective elevations is constant everywhere.

It is advantageous if the axial dimension of the center section of the pin-shaped pivoting element and the depth of the depression are matched to one another in such a way that the contact steps/contact steps formed by the radially widened center section of the pivoting element or by the push-on ring/sleeve continue to retain their stop and spacing function as described above, i.e. are arranged at the level of the elevations.

It would also be advantageous if the at least one depression/groove extends over the entire width of the guide section of the male instrument part (without frame formation), which has a particularly favorable effect on preventing seizure and also on disinfection.

There are further advantages if the area of the guide section distally relative to the depression/groove forms at least one front guide surface (elevation) which is prepared to be in contact with at least one of the inner surfaces of the hollow volume and the area of the guide section proximally relative to the depression/groove forms at least one rear guide surface (elevation) which is prepared to be in contact with at least one of the inner surfaces of the hollow volume. This means that not only the geometry of the depression, but also that of the guide surfaces/elevations is flexible and adaptable. At this point, it must be pointed out that the groove/depression and the resulting elevations do not have to be necessarily formed on a support side of the male instrument part, but can also be formed (in mirror-inverted fashion) on the other, turned-away support side of the male instrument part. The geometry of both grooves is identical or different.

Accordingly, the/each support side consisting of the recess and the resulting elevations on both sides of the recess can be designed variably in the entire coupling/hinge area. The male instrument part and the female instrument part contact each other only in the areas of the elevations which are partly determined by the geometry of the depression. The further contact necessary for an even guidance during pivoting is achieved by the center section and the steps of the pivoting element and the inner sides of the hollow volume.

Along a longitudinal axis of the instrument, which extends from a distal handle area to a proximal instrument engagement area (jaw part) formed by the instrument branches, a contact sliding surface is formed between the male and female instrument part at three points/sections of the upper side and at three points/sections of the underside of the male instrument part: at the anterior/distal elevation, at the respective axial step of the pivoting element and at the posterior/proximal elevation of the two contact sides of the male instrument part.

The groove/depression can be machined in the guide section as a milled recess that extends transversely to the longitudinal axis of the surgical instrument, making the production of the male instrument part cost- and time-efficient. Furthermore, manufacturing variations in terms of tolerance can be kept to a minimum.

If the bolt/pin-shaped pivoting element has a one-piece design and the upper (end) section of the pivoting element and the lower (end) section of the pivoting element are formed to be cylindrical, the object according to the invention of the pivoting element, namely a low-friction swiveling of the instrument parts relative to each other with simultaneous spacing of the hollow volume, can be realized particularly well.

Also a two-part design of the pivoting element, in which the upper (end) section of the pivoting element and the lower (end) section of the pivoting element are formed to be cylindrical, whereas the radially widened center section is formed by a push-on sleeve, is part of the invention as an advantageous embodiment. In the case of a two-part pivoting element, it would be appropriate to manufacture the two parts from different materials. The upper and lower (end) sections can be designed in one piece as rotationally symmetrical pin/stud and the center section as ring/sleeve with an opening through which the pin extends. A material combination of pin and ring, for example ceramic and austenite, is conceivable.

It would also be advantageous if the center section of the pivoting element is cylindrical. It thus forms a surface contact with an opening in the guide section of the male part of the instrument, which results in an additional robust guide. Moreover, the pivoting element can thus be designed as a stepped rivet, which can be produced reliably and cost-effectively.

A spherical/crowned design of the center section of the pivoting element is also possible. This has advantages when it comes to cleaning/lubrication, since due to the at least one depression/groove formed in the guide section of the male part, the spherical center section allows the two instrument parts to be opened three-dimensionally, especially if the surgical instrument is swiveled open by approx. 70° to 110°, preferably approx. 90°. This increases the mobility/flexibility of the instrument at least in the range of this swivel angle, which has a positive effect on its basic handling and thus many aspects.

The pivoting element may preferably be a rivet. It is also advantageous to manufacture the pivoting element and the branches of the instrument from different materials. An example is the material combination X40Cr13/X20Cr13, but this is not to be regarded as restrictive.

With regard to the depression/groove of the guide section of the male instrument part, it has to be considered that the guide surfaces which are in contact with the box-shaped hollow volume of the female instrument part are sufficiently large. A swiveling of the instrument parts (male and female instrument part) of up to 60° with robust and precise guidance to each other is easily possible with the guide surfaces' size according to the invention.

The terms 'top' and 'bottom' in the context of this application should be understood while referring to the following drawings in which they are marked with reference signs. Of course, when the instrument is rotated, an upper surface may point downwards or vice versa. Therefore, they serve only to differentiate the surfaces from each other and have no geometric validity in an absolute reference system.

BRIEF DESCRIPTION OF THE DRAWING FIGURES

The invention is explained in more detail below using a preferred exemplary embodiment with reference to the accompanying Figures wherein:

FIG. 1b is an exploded view of the surgical instrument from FIG. 1a;

The Figures are merely schematic in nature and serve exclusively to understand the invention. Identical elements have the same reference marks and can be exchanged with each other.

DETAILED DESCRIPTION

Figure 1A:
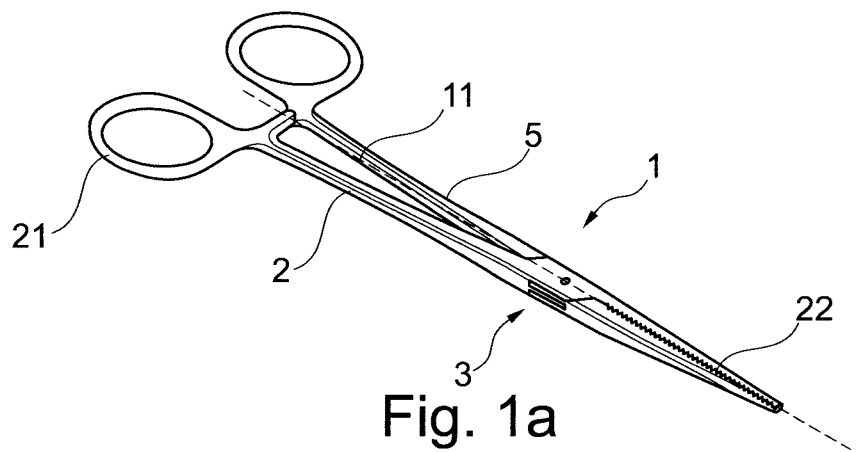
FIG. 1a is a perspective view of a surgical instrument according to a preferred exemplary embodiment of the present invention in an assembled state.

FIG. 1a shows a surgical instrument 1 of the branch design according to the invention in an assembled and closed/non-operated state (constructional position). A female instrument part or first instrument part 2 is coupled/hinged to a male instrument part or second instrument part 5 via a coupling/hinge region 3 in such a way that these can be pivoted relative to each other. The coupling region 3 is formed on the part of the first instrument part 2 via a hollow volume (hollow-volume push-through box) 4 and on the part of the second instrument part 5 via a guide section (push-through section) 6. This is preferably a push-through/box connection as it is known, for example, from DE 20 2011 000800 U1, so that reference can be made at this point to the disclosure there.

A manual actuation of a handle area 21 at the proximal end of each instrument part 2, 5 initiates a pivoting of the instrument parts 2, 5, which results in a corresponding movement of an operating/engagement area (branches) 22 at the distal end of each instrument part 2, 5 (also referred to as jaw part). An instrument longitudinal axis 11 extends along the closed instrument (constructional position) so as to intersect a hinge axis as described below and serves as orientation within the scope of this application. It extends from a proximal end, at which the handle area 21 is formed, to a distal end, at which the operating area (branches) 22 is formed. The operating area 22 is not limited to the clamp shape (grasping forceps) shown in FIG. 1a. Rather, it can assume all geometries in order to fulfil a surgical function including cutting blades, hooks and similar jaw parts.

Figure 1B:
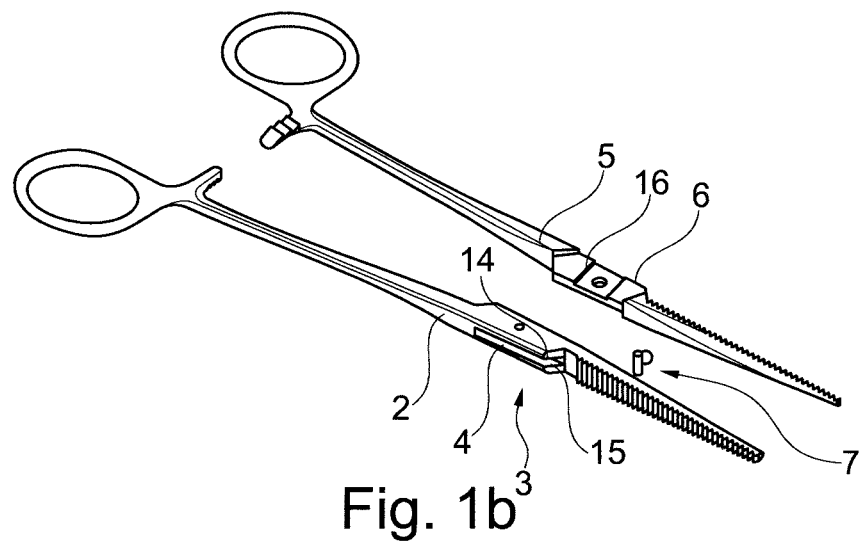

FIG. 1b shows the instrument 1 from FIG. 1a in an exploded view. A material flattening 16 is formed in the area of a central guide section 6 of the male instrument part 5, which defines the push-through section for the box-shaped hollow volume of the female instrument part 2. FIG. 1b shows the material flattening 16 in a preferred embodiment. On the upper side of the male instrument part 2 in its axial center section, two diametrically opposed milled recesses extend parallel to each other and transversely to the longitudinal axis 11, whereby at the edge of each milled recess two pivot-limiting edges spaced in the longitudinal direction of the instrument are formed, which, as can be seen from FIG. 1a, cooperate with the box-shaped hollow volume 4 in order, for example, to define a maximum closed position of the surgical instrument.

The material flattening 16 (i.e. the two milled recesses) also forms an additional groove or depression 16a in a region near a pivoting element 7, such as a pivoting bolt, which pivotally couples the two instrument parts 2, 5, and a respective elevation 16*b*, 16*c* in two regions, proximally and distally spaced from the pivoting element 8 as seen in the longitudinal direction of the instrument, which elevations are spaced apart from one another in the longitudinal direction of the instrument by the groove 16*a* formed in between and each define a guiding/sliding contact surface. The rear guide surface 16*b* is the area of the guide section 6 that lies proximal relative to the groove/depression 16*a*. The front guide surface 16*c* is the area of the guide section 6 that lies distally relative to the groove/depression 16*a*. The surface area ratios between the rear guide surface 16*b*, the groove/depression 16*a* and the front guide surface 16*c* are determined such that a robust guidance of the instrument parts 2, 5 to each other is possible, while at the same time the advantages according to invention apply, i.e. low sliding friction forces with good operability.

The front guide surface 16*c* and the rear guide surface 16*b* are of approximately the same size. The upwardly facing surfaces of the rear guide surface 16*b* and the front guide surface 16*c* are prepared to make a sliding contact with an upper inner surface 14 of the hollow volume 4. The downwardly facing surfaces of the rear guide surface 16*b* and the front guide surface 16*c* are prepared to make a sliding contact with a lower inner surface 15 of the hollow volume 4.

These sliding contacts on the front and rear guide surfaces 16*b*, 16*c* allow to achieve a reliable and uniform sliding guidance of the instrument parts 2, 5 relative to each other. In addition, the groove/depression 16*a* together with the upper and lower inner surfaces 14, 15 of the box-shaped hollow volume 4 forms a gap of predetermined gap width at each of the two milled recesses through which disinfectant can be introduced, which then spreads to the front and rear guide surfaces 16*b*, 16*c*. The depth of the depression in relation to that of the elevations 16*b*, 16*c* is preferably dimensioned such that the disinfectant introduced can spread well in the aforementioned gap.

The upper inner surface 14 is the upper surface of the hollow volume 4 pointing inwards. The lower inner surface 15 is diametrically opposed to the upper inner surface 14. Both the box-shaped hollow volume 4 and the guide section (push-through section) 6 are provided with a central through-hole, which overlap when the guide section 6 is inserted correctly through the box-shaped hollow volume 4, so that the pivoting element 7 (pivoting bolt) for the pivotal coupling of the two instrument parts 2 and 5 can be inserted.

Figure 2:
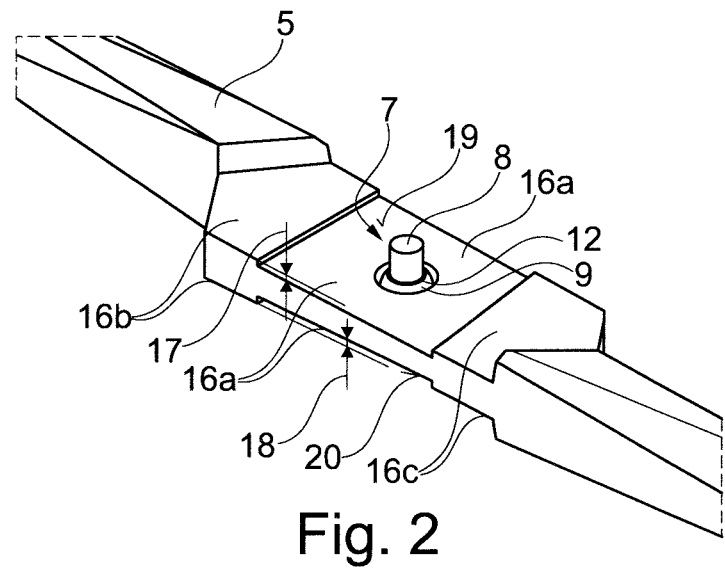
FIG. 2 is an enlarged view of a coupling/hinge area of a male instrument part of the surgical instrument from FIG. 1a, in which a pivoting element (pivoting pin) is arranged.

FIG. 2 shows an enlarged view of the coupling/hinge region 3, where the female instrument part 2 is not shown here for reasons of clarity. By means of the groove/depression 16*a*, the male instrument part 5 shown in FIG. 2 forms the above indicated upper/lower gap 17, 18 between the groove/depression 16*a* at each of the two milled recesses and the upper/lower inner surface 14, 15 of the hollow volume 4. The rear guide surface 16*b* has a polygonal base area. Preferably this is a pentagon with a rectangular base area. The front guide surface 16*c* has essentially the same shape with mirror-inverted orientation. The rectangular base area is therefore directly adjacent to the milled edge of the groove/depression 16.

Figure 3:
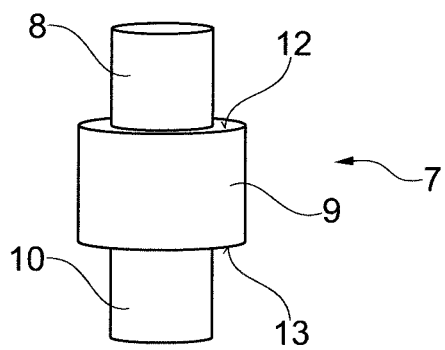
FIG. 3 shows a pivoting element/hinge pin/hinge bolt in a first embodiment according to the present invention.

FIG. 3 shows a concrete embodiment of a pivoting element 7 according to the preferred exemplary embodiment of the invention. In this embodiment, it may have a one-piece or also a two-piece design as can be taken from the exploded view according to FIG. 5. In any case, the pivoting element 7 is designed to be rotationally symmetrical and is or can be positively connected to the female and male instrument parts 2, 5. In this way, the two instrument parts 2, 5 can be swiveled about a rotation axis of the pivoting element 7.

In concrete terms, the pivoting element 7 is the swivel bolt with three axially subdivided sections, namely an axial center section 9 with a widened diameter and two axial end sections 8, 10 (on both sides of the center section 9) with comparatively constricted diameters. This means that the division into the three areas, i.e. upper section 8, center section 9 and lower section 10, is distinguished in this case by different diameters. The diameter of the upper and lower sections 7, 10 is smaller than that of the center section 9.

The present pivoting element 7 according to FIG. 3 is designed in one piece. According to the invention, a circumferential step/shoulder is formed in radial direction due to the diameter differences between the upper section 8 and the center section 9. This defines an upper contact step (upper stop, upper support edge) 12. The upper contact step 12 is prepared to contact the hollow volume 4 of the female branch 2 when the swivel bolt 7 is mounted. For this reason, the upper contact step 12 is particularly smooth and even.

The basic shape of the center section 9 according to FIG. 3 is a cylindrical one in the present embodiment. The center section 9, which in the present embodiment as well as in the others has a substantially comparable length along its axis of rotation in relation to the upper section 8 and the lower section 10, has, as mentioned above, a larger diameter than the upper and the lower sections 8, 10. The difference between those diameters lies in the range between a factor of 1.2 and 2.5.

Consequently, the center section 9 and the lower section 10 also form a contact step (lower stop, lower support edge) 13, as already described above for step 12. The step 13 between the lower section 10 and the center section 9 is therefore referred to as the lower contact step 13. Similar to the upper step 12, the lower step has the function of contacting the hollow volume 4 of the female branch 2 in the assembled state 2. The lower step 13 and the upper step 12 have an identical shape and are plane-parallel to each other.

Figure 4:
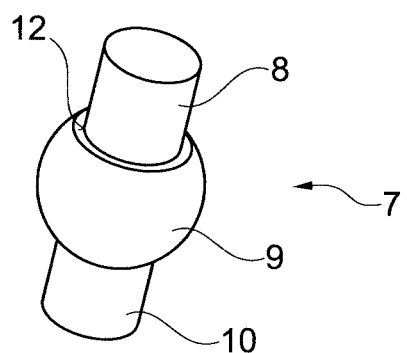
FIG. 4 shows a pivoting element/hinge pin/hinge bolt in a second embodiment of the present invention.

FIG. 4 shows the pivoting element 7 in another one-piece embodiment of the present invention. Here too, an upper contact step 12 and a lower contact step 13 are formed. In contrast to the embodiment according to FIG. 3, however, the shape of the center section 9 between the upper step 12 and the lower step 13 is crowned (radially convex) in the present embodiment. In this section, the center section 9 therefore has a spherical shape.

For both embodiments according to FIGS. 3 and 4, however, it is provided that the axial distance between the upper and lower contact steps 12, 13 corresponds to the parallel distance between the upper and lower inner surfaces 14, 15 of the box-shaped hollow volume 4 of the female instrument part 2. By equating these two distances, uniform guidance of the female instrument part 2 relative to the male instrument part 5 is ensured, since all contact surfaces (upper and lower inner surfaces 14, 15) of the hollow volume 4 come into sliding contact both with the sliding surfaces on the elevations 16*b*, 16*c* of the male instrument part 5 and the contact steps 12, 13 of the pivoting pin.

Analogous to the upper gap 17, there is a lower gap 18, as can be clearly seen in FIG. 2. For the lower gap, the same characteristics apply as for the upper gap 17, except that it is designed in an opposite direction on a lower surface 16*a* of the groove/depression 16*a*.

In the present embodiment, the center section 9 of the pivoting element 7 has a preferably spherical design between the upper contact step 12 and the lower contact step 13. In this way, a kind of ball joint bearing of the pivoting element 7 is realized in the guide section 6 of the male instrument part 5. Due to the groove/depression 16a, a three-dimensional movement/swiveling/tilting of the female instrument part 2 relative to the male instrument part 5 is therefore possible in a certain relative rotational position of both instrument parts 2, 5. This swiveling/tilting mainly serves to increase the disinfectability/cleanability of the surgical instrument 1, especially in the hinge region 3 of both instrument parts 2, 5. It also increases their flexibility.

The one-piece pivoting element 7 may be made from X40Cr 13, for example, and can be hardened. Because the pivoting element 7 is made of a material different from that of the instrument parts 2, 5, seizing of the two instrument parts 2, 5 is made even more difficult.

Figure 5:
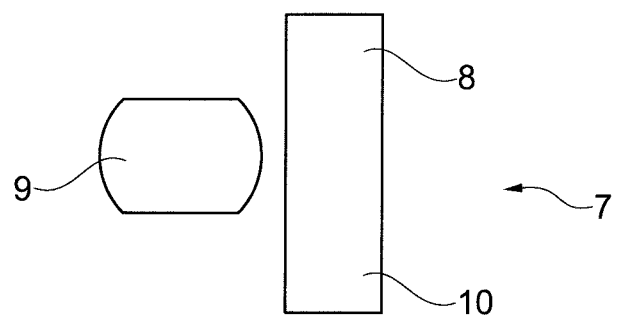
FIG. 5 shows a pivoting element/hinge pin/hinge bolt in a third embodiment of the present invention.

A further embodiment of the pivoting element 7 is shown in FIG. 5. This is a two-piece pivoting element 7. The term "two-piece" means that the pivoting element 7 consists of a pin/bolt and a ring/sleeve which is fitted onto the (hinge) pin. The pin forms the upper section 8 at its upper end and the lower section 10 at its lower end. The area of the pin between the upper and lower sections 8, 10 is prepared to receive the ring/sleeve functionally forming the center section 9. With regard to its geometry, the two-piece design of the pivoting element 7 does not differ from the one-piece design. In this way, it is possible to manufacture the ring and the pin from two different materials. An example of this is the combination of austenite and ceramic.

The geometry of the pivoting element 7 is freely selectable. According to the invention, however, the upper and lower steps 12, 13 are necessary in order to achieve the advantages of the stable swivel guide. The remaining design of the center section 9 or also of the lower section 10 and the upper section 8 can be varied depending on the case of application in order to optimally adapt the pivoting element 7 to the prevailing conditions.

The invention claimed is:

1. A surgical instrument comprising a first instrument part and a second instrument part coupled to one another in a hinge-like manner, each instrument part comprising a coupling region and at least one abutment side in the coupling region, on which the first instrument part and the second instrument part bear against one another in a pivotally sliding manner about a hinge pin, the hinge pin arranged or formed in the coupling region, wherein at least one of the at least one abutment side of the first instrument part and/or the second instrument part has a superficial material removal that forms at least one recess in a region close to the hinge pin, the at least one recess defined by a first pivot limiting edge, a second pivot limiting edge, and a bottom surface extending between the first pivot limiting edge and second pivot limiting edge, the bottom surface defining a first raised portion, a second raised portion and a depression with a predetermined groove depth between the first raised portion and second raised portion, the first raised portion and second raised portion extending in a longitudinal direction of the surgical instrument on both sides of the hinge pin in regions of the at least one of the at least one abutment side remote from the hinge pin, the first raised portion and second raised portion enclosing the depression between the raised portions in the longitudinal direction of the surgical instrument, wherein the hinge pin in a constructional position has at least one support edge that acts in an axial direction thereof at a level of the raised portions.

2. The surgical instrument according to claim 1, wherein a three-point sliding bearing is created by the first raised portion, the second raised portion, and the at least one support edge on the hinge pin.

3. The surgical instrument according to claim 1, wherein the at least one support edge on a hinge pin side is formed in a one-piece design by a center section, thickened or radially widened relative to at least one axial end section or in a two-piece design by a sleeve, pushed onto the hinge pin.

4. The surgical instrument according to claim 3, wherein the center section or the push-on sleeve has a crowned spherical contour on a shell side in such a way that a hinge contact between the second instrument part and the hinge pin is linear.

5. The surgical instrument according to claim 1, wherein the first instrument part comprises a female instrument part and forms in its respective hinge region a push-through box with two diametrically facing, inner abutment sides, and the second instrument part comprises a male instrument part and forms in its respective hinge region a push-through section with two diametrically opposed outer abutment sides that are in sliding contact with inner abutment sides of the first instrument part, wherein the at least one recess comprises a recess on each outer abutment side of the second instrument part.

6. The surgical instrument according to claim 5, wherein the at least one support edge comprises two axially spaced support edges defined by the hinge pin in the constructional position at a level of the respective raised portions against which the inner abutment sides of the second instrument part bear in a pivotally sliding manner.

7. The surgical instrument according to claim 1, wherein the at least one support edge is configured to contact at least one abutment side of the first instrument part or second instrument part.

* * * * *